United States Patent
Gill et al.

(10) Patent No.: US 10,398,576 B2
(45) Date of Patent: Sep. 3, 2019

(54) PROSTHETIC FEEDBACK APPARATUS AND METHOD

(75) Inventors: Hugh Gill, Strathclyde (GB); Sethu Vijayakumar, Lothian (GB); Ian Saunders, Yorkshire (GB)

(73) Assignees: Touch Bionics Limited, Livingston (GB); The University Court of the University of Edinburgh, Edinburgh (GB)

( * ) Notice: Subject to any disclaimer, the term of this patent is extended or adjusted under 35 U.S.C. 154(b) by 188 days.

(21) Appl. No.: 14/235,282

(22) PCT Filed: Aug. 17, 2012

(86) PCT No.: PCT/GB2012/052021
§ 371 (c)(1),
(2), (4) Date: May 13, 2014

(87) PCT Pub. No.: WO2013/024306
PCT Pub. Date: Feb. 21, 2013

(65) Prior Publication Data
US 2014/0324189 A1   Oct. 30, 2014

(30) Foreign Application Priority Data

Aug. 17, 2012 (GB) .................................. 1114264.3

(51) Int. Cl.
*A61F 2/58* (2006.01)
*A61F 2/68* (2006.01)
(Continued)

(52) U.S. Cl.
CPC ................ *A61F 2/68* (2013.01); *A61F 2/583* (2013.01); *A61F 2/588* (2013.01);
(Continued)

(58) Field of Classification Search
CPC .......... A61F 2/583; A61F 2/586; A61F 2/588; A61F 2/68; A61F 2002/587;
(Continued)

(56) References Cited

U.S. PATENT DOCUMENTS 1,507,682 A    9/1924  Pecorella et al.
2,445,711 A    7/1948  Fitch
(Continued)

FOREIGN PATENT DOCUMENTS

CN    1803413    7/2006
DE    309 367    11/1918
(Continued)

OTHER PUBLICATIONS

Martinez-Villapando, Ernesto. Agonist-antagonist active knee prostehsis: A preliminary study in level-ground walking. Journal of Rehabilitation Research & Development. vol. 46, No. 3, 2009. pp. 361-374.*
(Continued)

*Primary Examiner* — Christie L Bahena
(74) *Attorney, Agent, or Firm* — Knobbe, Martens, Olson & Bear, LLP

(57) ABSTRACT

A prosthesis (1) or an orthosis and method of operating the same. The prosthesis or orthosis comprising a moveable component (2), a motor (7) operable to move the component, wherein the motor has at least one operating parameter, the application of which to the motor results in the component having at least one operating condition; and an electronic device (28) operable to: determine at least one operating parameter of the motor and determine at least one instantaneous operating condition of the component from a predetermined operating profile of the motor and component and the determined at least one operating parameter of the motor, the predetermined operating profile of the motor and component being based on one or more operating parameter inputs to the motor and one or more resulting operating condition outputs of the component.

20 Claims, 3 Drawing Sheets

(51) Int. Cl.
*A61F 2/70* (2006.01)
*B25J 15/00* (2006.01)

(52) U.S. Cl.
CPC ... *B25J 15/0009* (2013.01); *A61F 2002/6827* (2013.01); *A61F 2002/6836* (2013.01); *A61F 2002/701* (2013.01); *A61F 2002/704* (2013.01)

(58) Field of Classification Search
CPC ........ A61F 2002/6827; A61F 2002/769; A61F 2002/5061; A61F 2002/5059; A61F 2002/5058; B25J 15/0009
See application file for complete search history.

(56) References Cited

U.S. PATENT DOCUMENTS

| | | |
|---|---|---|
| 2,477,463 A | 7/1949 | Otterman |
| 2,482,555 A | 9/1949 | Otterman |
| 2,508,156 A | 5/1950 | Gillman |
| 2,516,791 A | 7/1950 | Motis et al. |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraioli |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A * | 11/1986 | Childress ............... A61F 2/588 623/25 |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,775 A | 7/1992 | Chen |
| 5,246,463 A * | 9/1993 | Giampapa ............... A61B 5/12 623/24 |
| 5,252,102 A | 10/1993 | Singer et al. |
| 5,255,188 A * | 10/1993 | Telepko ................ A61H 1/02 601/23 |
| 5,387,245 A | 2/1995 | Fay et al. |
| 5,413,454 A | 5/1995 | Movsesian |
| 5,413,611 A * | 5/1995 | Haslam, II ............. A61F 2/583 623/24 |
| 5,498,472 A | 3/1996 | Gold |
| 5,581,166 A | 12/1996 | Eismann et al. |
| 5,785,960 A | 7/1998 | Rigg et al. |
| 5,851,194 A | 12/1998 | Fratrick |
| 5,852,675 A | 12/1998 | Matsuo et al. |
| 5,888,213 A | 3/1999 | Sears et al. |
| 5,888,246 A | 3/1999 | Gow |
| 5,900,714 A * | 5/1999 | Dubhashi ............... H02P 6/28 318/811 |
| 6,111,973 A | 8/2000 | Holt et al. |
| 6,175,962 B1 | 1/2001 | Michelson |
| 6,223,615 B1 | 5/2001 | Huck |
| 6,344,062 B1 | 2/2002 | Abboudi et al. |
| 6,361,570 B1 | 3/2002 | Gow |
| 6,660,043 B2 | 12/2003 | Kajitani et al. |
| 6,786,112 B2 | 9/2004 | Ruttor |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,640,680 B1 | 1/2010 | Castro |
| 7,823,475 B2 | 11/2010 | Hirabayashi et al. |
| 7,867,287 B2 | 1/2011 | Puchhammer |
| 7,922,773 B1 | 4/2011 | Kuiken |
| 8,016,893 B2 | 9/2011 | Weinberg et al. |
| 8,100,986 B2 | 1/2012 | Puchhammer et al. |
| 8,197,554 B2 | 6/2012 | Whiteley et al. |
| 8,257,446 B2 | 9/2012 | Puchhammer |
| 8,337,568 B2 | 12/2012 | Macduff |
| 8,491,666 B2 | 7/2013 | Schulz |
| 8,579,991 B2 | 11/2013 | Puchhammer |
| 8,593,255 B2 | 11/2013 | Pang et al. |
| 8,657,887 B2 | 2/2014 | Gill |
| 8,662,552 B2 | 3/2014 | Torres-Jara |
| 8,663,339 B2 | 3/2014 | Inschlag et al. |
| 8,690,963 B2 | 4/2014 | Puchhammer |
| 8,696,763 B2 | 4/2014 | Gill |
| 8,808,397 B2 | 8/2014 | Gow |
| 8,828,096 B2 | 9/2014 | Gill |
| 8,986,395 B2 | 3/2015 | McLeary |
| 8,995,760 B2 | 3/2015 | Gill |
| 9,278,012 B2 | 3/2016 | Gill |
| 9,387,095 B2 | 7/2016 | McLeary et al. |
| 9,402,749 B2 | 8/2016 | Gill et al. |
| 9,463,100 B2 | 10/2016 | Gill |
| 9,720,515 B2 | 8/2017 | Wagner et al. |
| 9,839,534 B2 | 12/2017 | Lipsey et al. |
| 9,999,522 B2 | 6/2018 | Gill |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2004/0002672 A1 | 1/2004 | Carlson |
| 2004/0078091 A1 | 4/2004 | Elkins |
| 2004/0078299 A1 | 4/2004 | Down-Logan et al. |
| 2004/0181289 A1 | 9/2004 | Bedard et al. |
| 2004/0182125 A1 | 9/2004 | McLean |
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0175681 A1 | 8/2007 | King et al. |
| 2007/0230832 A1 | 10/2007 | Usui et al. |
| 2007/0260328 A1 | 11/2007 | Bertels et al. |
| 2008/0058668 A1 | 3/2008 | Seyed Momen et al. |
| 2008/0146981 A1 | 6/2008 | Greenwald et al. |
| 2008/0215162 A1* | 9/2008 | Farnsworth ........ A61B 5/04888 623/57 |
| 2008/0260218 A1 | 10/2008 | Smith et al. |
| 2008/0262634 A1 | 10/2008 | Puchhammer |
| 2009/0213379 A1 | 8/2009 | Carroll et al. |
| 2010/0016990 A1 | 1/2010 | Kurtz |
| 2010/0036507 A1 | 2/2010 | Gow |
| 2010/0116070 A1 | 5/2010 | Kim |
| 2010/0274365 A1 | 10/2010 | Evans et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |

(56) References Cited

U.S. PATENT DOCUMENTS

| | | | |
|---|---|---|---|
| 2012/0004884 A1 | 1/2012 | Fillol et al. | |
| 2012/0014571 A1 | 1/2012 | Wong et al. | |
| 2012/0061155 A1* | 3/2012 | Berger | B25J 5/007 180/21 |
| 2012/0099788 A1 | 4/2012 | Bhatti et al. | |
| 2012/0109337 A1 | 5/2012 | Schulz | |
| 2012/0123558 A1 | 5/2012 | Gill | |
| 2012/0204665 A1 | 8/2012 | Baudasse | |
| 2012/0280812 A1 | 11/2012 | Sheikman et al. | |
| 2012/0286629 A1 | 11/2012 | Johnson et al. | |
| 2012/0303136 A1 | 11/2012 | Macduff | |
| 2012/0330439 A1 | 12/2012 | Goldfarb et al. | |
| 2013/0041476 A1 | 2/2013 | Schulz | |
| 2013/0053984 A1* | 2/2013 | Hunter | A61F 2/583 623/64 |
| 2013/0076699 A1 | 3/2013 | Spencer | |
| 2013/0144197 A1 | 6/2013 | Ingimundarson et al. | |
| 2013/0253705 A1 | 9/2013 | Goldfarb et al. | |
| 2013/0268094 A1 | 10/2013 | Van Wiemeersch | |
| 2014/0236314 A1 | 8/2014 | Van Wiemeersch | |
| 2014/0371871 A1 | 12/2014 | Farina et al. | |
| 2015/0142082 A1 | 5/2015 | Simon et al. | |
| 2015/0216679 A1 | 8/2015 | Lipsey et al. | |
| 2015/0216681 A1 | 8/2015 | Lipsey et al. | |
| 2015/0374515 A1 | 12/2015 | Meijer et al. | |
| 2016/0287422 A1 | 10/2016 | Kelly et al. | |
| 2017/0007424 A1 | 1/2017 | Gill | |
| 2017/0049586 A1 | 2/2017 | Gill et al. | |
| 2017/0281368 A1 | 10/2017 | Gill | |
| 2018/0064563 A1 | 3/2018 | Gill | |
| 2018/0071115 A1 | 3/2018 | Lipsey et al. | |
| 2018/0296368 A1 | 10/2018 | Gill | |

FOREIGN PATENT DOCUMENTS

| | | | |
|---|---|---|---|
| DE | 24 34 834 | | 2/1976 |
| DE | 198 54 762 | | 6/2000 |
| DE | 101 05 814 | | 9/2002 |
| DE | 203 15 575 | | 1/2004 |
| DE | 10 2012 009 699 | | 11/2013 |
| EP | 0145504 | | 6/1985 |
| EP | 0 219 478 | | 4/1987 |
| EP | 0 256 643 | | 2/1988 |
| EP | 0 484 173 | | 5/1992 |
| EP | 0 947 899 | | 10/1999 |
| EP | 0 968 695 | | 1/2000 |
| EP | 1043003 | | 10/2000 |
| EP | 1 617 103 | | 1/2006 |
| EP | 2 532 927 | | 12/2012 |
| EP | 2 612 619 | | 7/2013 |
| GB | 326 970 | | 3/1930 |
| GB | 607 001 | | 2/1947 |
| GB | 1 386 942 | | 3/1975 |
| GB | 1 510 298 | | 5/1978 |
| GB | 1585256 | | 2/1981 |
| GB | 2 067 074 | | 7/1981 |
| GB | 2 146 406 | | 4/1985 |
| GB | 2 357 725 A | | 7/2001 |
| GB | 2444679 | | 6/2008 |
| JP | 53-11456 | | 2/1978 |
| JP | 53-094693 | | 8/1978 |
| JP | 07-174631 | | 7/1995 |
| JP | 2001082913 | * 3/2001 | G01B 7/30 |
| JP | 2001-299448 | | 10/2001 |
| JP | 2002-131135 | | 5/2002 |
| JP | 2002-310242 | | 10/2002 |
| JP | 2003-134526 | | 5/2003 |
| JP | 2004-073802 | | 3/2004 |
| JP | 2004-224280 | | 8/2004 |
| WO | 95/24875 | | 9/1995 |
| WO | WO 96/023643 | | 8/1996 |
| WO | WO 00/025840 | | 5/2000 |
| WO | 00/69375 | | 11/2000 |
| WO | WO 01/004838 | | 1/2001 |
| WO | WO 02/049534 | | 6/2002 |
| WO | 03/017878 | | 3/2003 |
| WO | 03/017880 | | 3/2003 |
| WO | WO 03/017877 | | 3/2003 |
| WO | 2006/069264 | | 6/2006 |
| WO | WO 2006/058190 | | 6/2006 |
| WO | WO 2006/078432 | | 7/2006 |
| WO | WO 2006/086504 | | 8/2006 |
| WO | WO 2006/092604 | | 9/2006 |
| WO | WO 2006/110790 | | 10/2006 |
| WO | 2007/063266 | | 6/2007 |
| WO | 2007/076764 | | 7/2007 |
| WO | 2007/076765 | | 7/2007 |
| WO | 2007/127973 | | 11/2007 |
| WO | WO 2007/126854 | | 11/2007 |
| WO | 2008/044207 | | 4/2008 |
| WO | WO 2008/044052 | | 4/2008 |
| WO | 2008/098059 | | 8/2008 |
| WO | 2008/098072 | | 8/2008 |
| WO | WO 2008/092695 | | 8/2008 |
| WO | WO 2009/011682 | | 1/2009 |
| WO | 2010/018358 | | 2/2010 |
| WO | WO 2010/051798 | | 5/2010 |
| WO | WO 2010/149967 | | 12/2010 |
| WO | 2011/001136 A2 | | 1/2011 |
| WO | 2011/022569 A1 | | 2/2011 |
| WO | 2011/036473 | | 3/2011 |
| WO | WO 2011/036626 | | 3/2011 |
| WO | WO 2011/088964 | | 7/2011 |
| WO | 2011/107778 | | 9/2011 |
| WO | WO 2011/143004 | | 11/2011 |
| WO | WO 2015/120076 | | 8/2015 |
| WO | WO 2015/120083 | | 8/2015 |
| WO | WO 2016/051138 | | 4/2016 |

OTHER PUBLICATIONS

DC Circuit Theory. Electronics Tutorials. Date verified by the wayback machine Apr. 23, 2013.*
Translation of JP2001082913.*
Connolly, "Prosthetic hands from Touch Bionics," Industrial Robot: An International Journal, 35(4):290-293, 2008.
Stix, "Phantom Touch: Imbuing a Prosthesis with Manual Dexterity," Scientific American, Oct. 1998, pp. 41 and 44.
Search Report for GB Application No. GB0916895.6 dated Mar. 17, 2010, 5 pages.
Search Report for GB Application No. GB0910920.8 dated Mar. 26, 2010, 3 pages.
PCT International Search Report for PCT International Application No. PCT/GB2013/051961, dated Dec. 11, 2013, 5 pages.
PCT International Search Report for PCT International Application No. PCT/GB2012/052111, dated Nov. 26, 2012, 5 pages.
PCT International Preliminary Report on Patentability for PCT International Application No. PCT/GB2010/051529, dated Apr. 5, 2012, 7 pages.
PCT International Preliminary Report on Patentability for PCT International Application No. PCT/GB2011/050368, dated Sep. 13, 2012, 7 pages.
PCT International Search Report and Written Opinion of International Searching Authority for PCT International Application No. PCT/GB2011/050368, dated Jun. 21, 2011, 11 pages.
PCT International Search Report and Written Opinion of International Searching Authority for PCT International Application No. PCT/GB2010/001232, dated Oct. 6, 2010, 9 pages.
PCT International Preliminary Report on Patentability for PCT International Application No. PCT/GB2010/001232, dated Jan. 4, 2012, 6 pages.
PCT International Search Report and Written Opinion of International Searching Authority for PCT International Application No. PCT/GB2010/051529, dated Jan. 4, 2011, 11 pages.
International Search Report for PCT International Application No. PCT/GB2012/052021; dated May 3, 2013; (5 pgs.).
Written Opinion of the International Searching Authority for PCT International Patent Application No. PCT/GB2012/052021 filed on Aug. 17, 2012; date of search completion Nov. 15, 2012; search dated May 3, 2013; (6 pgs).

(56) References Cited

OTHER PUBLICATIONS

Matthew S. Trachtenberg et al. "Radio frequency identification, An innovative solution to guide dexterous prosthetic hands" 33rd Annual International Conference of the IEEE EMBS, Boston, Massachusetts, USA, [Aug. 30-Sep. 3, 2011], 4 pages.

Luke Osborn et al. "Utilizing tactile feedback for biomimetic grasping control in upper limb prostheses" Department of Biomedical Engineering, Johns Hopkins University, Baltimore, USA, [2013], 4 pages.

Alessandra Pedrocchi et al. "MUNDUS project: Multimodal Neuroprosthesis for daily Upper Limb Support" Journal of Neuroengineering and Rehabilitation, [2013], 10:66, http://www.jneuroengrehab.com/content/10/1/66, 20 pages.

Michael Mace et al. "Augmenting neuroprosthetic hand control through evaluation of a bioacoustic interface" IEEE/RSJ International Conference on Intelligent Robots and Systems (IROS), Tokyo, Japan, [Nov. 3-7, 2013], 7 pages.

Albu-Schaffer et al., "Soft Robotics", IEEE Robotics & Automation Magazine, Sep. 2008, vol. 15, No. 3, pp. 20-30.

Bellman et al., "SPARKy 3: Design of an Active Robotic Ankle Prosthesis with Two Actuated Degrees of Freedom Using Regenerative Kinetics", in Proceedings of the $2^{nd}$ Biennial IEEE/RAS-EMBS International Conference on Biomedical Robotics and Biomechatronics, Oct. 19-22, 2008, Scottsdale, AZ, pp. 511-516.

Belter et al., "Mechanical Design and Performance Specifications of Anthropomorphic Prosthetic Hands: A Review", JRRD, Jan. 2013, vol. 50, No. 5, pp. 599-618.

Biddiss et al., "Consumer Design Priorities for Upper Limb Prosthetics", Disability and Rehabilitation: Assistive Technology, Nov. 2007, vol. 2, No. 6, pp. 346-357.

Biddiss et al., "Upper Limb Prosthesis Use and Abandonment: A Survey of the Last 25 Years", Prosthetics and Orthotics International, Sep. 2007, vol. 31, No. 3, pp. 236-257.

Biddiss et al., "Upper-Limb Prosthetics: Critical Factors in Device Abandonment", American Journal of Physical Medicine & Rehabilitation, Dec. 2007, vol. 86, No. 12, pp. 977-987.

Chicoine et al., "Prosthesis-Guided Training of Pattern Recognition-Controlled Myoelectric Prosthesis", in Proceedings of the $34^{th}$ Annual International Conference of the IEEE EMBS, San Diego, CA, Aug. 28-Sep. 1, 2012, pp. 1876-1879.

Childress et al., "Control of Limb Prostheses", American Academy of Orthopaedic Surgeons, Chapter 12, pp. 173-195, 2004.

Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.

Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.

Controzzi et al., "Miniaturized Non-Back-Drivable Mechanism for Robotic Applications", Mechanism and Machine Theory, Oct. 2010, vol. 45, No. 10, pp. 1395-1406.

Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.

Dechev et al., "Multiple Finger, Passive Adaptive Grasp Prosthetic Hand", Mechanism and Machine Theory, Oct. 1, 2001, vol. 36, No. 10, pp. 1157-1173.

Dellorto, Danielle, "Bionic Hands Controlled by iPhone App", CNN, Apr. 12, 2013, pp. 4 http://www.cnn.com/2013/04/12/health/bionic-hands.

"DuPont Engineering Design—The Review of DuPont Engineering Polymers in Action", http://www.engpolymer.co/kr/x_data/magazine/engdesign07_2e.pdf, Feb. 2007, pp. 16.

Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.

Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.

Gaine et al., "Upper Limb Traumatic Amputees. Review of Prosthetic Use", The Journal of Hand Surgery, Feb. 1997, vol. 22B, No. 1, pp. 73-76.

Heckathorne, Craig W., "Components for Electric-Powered Systems", American Academy of Orthopaedic Surgeons, Chapter 11, pp. 145-171, 2004.

Hojjat et al., "A Comprehensive Study on Capabilities and Limitations of Roller-Screw with Emphasis on Slip Tendency", Mechanism and Machine Theory, 2009, vol. 44, No. 10, pp. 1887-1899.

Hsieh et al., "Dynamics Analysis of Cycloidal Speed Reducers with Pinwheel and Nonpinwheel Designs", ASME J. Mech. Des. Jun. 2014, vol. 136, No. 9, p. 091008.

Jebsen et al., "An Objective and Standardized Test of Hand Function", Archives of Physical Medicine and Rehabilitation, Jun. 1969, vol. 50, No. 6, pp. 311-319.

Johannes et al., "An Overview of the Developmental Process for the Modular Prosthetic Limb," John Hopkins APL Technical Digest, 2011, vol. 30, No. 3, pp. 207-216.

Kent et al., "Electromyogram Synergy Control of a Dexterous Artificial Hand to Unscrew and Screw Objects", Journal of Neuroengineering and Rehabilitation, 2014, vol. 11, No. 1, pp. 1-20.

Kermani et al., "Friction Identification and Compensation in Robotic Manipulators", IEEE Transactions on Instrumentation and Measurement, Dec. 2007, vol. 56, No. 6, pp. 2346-2353.

Kuiken et al., "Targeted Muscle Reinnervation for Real-Time Myoelectric Control of Multifunction Artificial Arms", JAMA, Feb. 11, 2009, vol. 301, No. 6, pp. 619-628.

Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.

Majd et al., "A Continuous Friction Model for Servo Systems with Stiction", in Proceedings of the IEEE Conference on Control Applications, 1995, pp. 296-301.

Maxon Precision Motors, Inc., "Maxon Flat Motor: EX 10 flat 10 mm, brushless, 0.2 Watt", Specification, May 2011, p. 181.

Maxon Precision Motors, Inc., "Maxon EX Motor: EC10 10 mm, brushless, 8 Watt", Specification, May 2011, p. 140.

Miller et al., "Summary and Recommendations of the Academy's State of the Science Conference on Upper Limb Prosthetic Outcome Measures", Journal of Prosthetics Orthotics, 2009, vol. 21, pp. 83-89.

Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.

Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.

Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.

Pinzur et al., "Functional Outcome Following Traumatic Upper Limb Amputation and Prosthetic Limb Fitting", The Journal of Hand Surgery, Sep. 5, 1994. vol. 19A, pp. 836-839.

Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.

Raspopovic et al., "Restoring Natural Sensory Feedback in Real-Time Bidirectional Hand Prostheses", Science Translational Medicine, Feb. 5, 2014, vol. 6, No. 222, pp. 1-10.

Resnik et al., "The DEKA Arm: Its Features, Functionality, and Evolution During the Veterans Affairs Study to Optimize the DEKA Arm", Prosthetics and Orthotics International, 2014, vol. 38, No. 6, pp. 492-504.

(56) References Cited

OTHER PUBLICATIONS

Scheme et al., "Electromyogram Pattern Recognition for Control of Powered Upper-Limb Prostheses: State of the Art and Challenges for Clinical Use", Journal of Rehabilitation Research & Development (JRRD), 2011, vol. 48, No. 6, pp. 643-659.
Scheme et al., "Motion Normalized Proportional Control for Improved Pattern Recognition-Based Myoelectic Control", IEEE Transactions on Neural Systems and Rehabilitation Engineering, Jan. 2014, vol. 22, No. 1, pp. 149-157.
Sensinger et al., "Cycloid vs. Harmonic Drives for use in High Ratio, Single Stage Robotic Transmissions", presented at the IEEE Conference on Robotics and Automation, Saint Paul, MN, USA, May 14-18, 2012, pp. 4130-4135.
Sensinger, "Efficiency of High-Sensitivity Gear Trains, such as Cycloid Drives", Journal of Mechanical Design, Jul. 2013, vol. 135, No. 7, pp. 071006-1-071006-9.
Sensinger et al., "Exterior vs. Interior Rotors in Robotic Brushless Motors", 2011 IEEE International Conference on Robotics and Automation (ICRA), IEEE, May 9-13, 2011, pp. 2764-2770.
Sensinger, "Selecting Motors for Robots Using Biomimetic Trajectories: Optimum Benchmarks, Windings, and other Considerations," in Proceedings of the IEEE Conference on Robotics and Automation, Anchorage, AL, USA, May 3-8, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.
Sutton et al., "Towards a Universal Coupler Design for Modern Powered Prostheses", Presented at the Myoelectric Controls Symposium Fredericton, New Brunswick, Canada, Aug. 14-19, 2011, pp. 5.
Tan et al., "A Neural Interface Provides Long-Term Stable Natural Touch Perception", Science Translational Medicine, Oct. 8, 2014, vol. 6, No. 257, pp. 1-11.
Tang, "General Concepts of Wrist Biomechanics and a View from Other Species", The Journal of Hand Surgery, European Volume, Aug. 2008, vol. 33, No. 4, pp. 519-525.
Toledo et al., "A Comparison of Direct and Pattern Recognition Control for a Two Degree-of-Freedom Above Elbow Virtual Prosthesis", in Proceedings $34^{th}$ Annual International Conference of the IEEE EMBS, 2012, pp. 4332-4335.
Weir, Ph.D., Richard D., "Design of Artificial Arms and Hands for Prosthetic Applications", Standard Handbook of Biomedical Engineering and Design, Chapter 32, 2009, vol. 2, pp. 537-598.
Wettels et al., "Grip Control Using Biomimetic Tactile Sensing Systems", IEEE/ASME Transactions on Mechatronics, Dec. 2009, vol. 14, No. 6, pp. 718-723.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.
Zampagni et al., "A Protocol for Clinical Evaluation of the Carrying Angle of the Elbow by Anatomic Landmarks", Journal of Shoulder and Elbow Surgery, 2008, vol. 17, No. 1, pp. 106-112.
Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
International Preliminary Report on Patentability and Written Opinion in Application No. PCT/GB2012/052021, dated Feb. 27, 2014.
Kyberd et al., "Two-Degree-of-Freedom Powered Prosthetic Wrist", Journal of Rehabilitation Research & Development, 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Grip Chips™ Datasheet, May 15, 2014, Issue 1, http://touchbionics.com/sites/default/files/files/Grip%20Chip%20datasheet%20May%202014.pdf, pp. 1.
"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.
Vilarino, Martin, "A Novel Wireless Controller for Switching among Modes for an Upper-Limb Prosthesis", The Academy Today, Jan. 2014, vol. 10, No. 1, pp. A-12 to A-15.

* cited by examiner

PROSTHETIC FEEDBACK APPARATUS AND METHOD

CROSS REFERENCE TO RELATED APPLICATIONS

This application is a national phase under 35 U.S.C. § 371 of International Application No. PCT/GB2012/052021 filed on Aug. 17, 2012, which claims priority to and benefit of GB Application No. 1114264.3 filed on Aug. 18, 2011, the entirety of these applications are incorporated by reference herein.

The present invention relates to a moveable component of a prosthesis or an orthosis and a method of operating the same.

Prosthetic hands with powered digits are known. For example, WO 2007/063266 and WO 2010/149967 disclose a prosthesis with a mechanically operable digit member that is moved by an electric motor. WO 2010/149967 discloses a method of controlling the operation of the digit member to increase the force applied thereby to an object.

The present inventor has appreciated shortcomings with known prostheses having motor driven digit members, such as those disclosed in WO 2007/063266 and WO 2010/149967.

According to a first aspect of the present invention there is provided a prosthesis or an orthosis comprising:
a moveable component;
a motor operable to move the component, wherein the motor has at least one operating parameter, the application of which to the motor results in the component having at least one operating condition; and
an electronic device operable to:
determine at least one operating parameter of the motor; and
determine at least one instantaneous operating condition of the component from a predetermined operating profile of the motor and component and the determined at least one operating parameter of the motor, the predetermined operating profile of the motor and component being based on one or more operating parameter inputs to the motor and one or more resulting operating condition outputs of the component.

The electronic device may be operable to determine at least one instantaneous operating parameter of the motor.

The predetermined operating profile of the motor and component may be based on a plurality of operating parameter inputs to the motor and a plurality of resulting operating condition outputs of the component.

The motor may be located inside the component.

The component may be a digit of a hand prosthesis. The component may be a finger or a thumb member of hand prosthesis. The motor may be located inside the digit of the hand prosthesis.

The component may be moveable with respect to a support body of the prosthesis or orthosis. The component may rotate and/or pivot with respect to the support body of the prosthesis or orthosis.

The motor may be an electric motor. The motor may be a direct current motor. The motor may be an AC motor, a DC motor, a brushed or brushless motor, a servo motor, a stepper motor, a linear motor or a worm gear motor.

The at least one operating parameter of the motor may include an electrical signal. The electrical signal may be in the form of an applied electrical current and/or voltage.

The at least one operating parameter of the motor may include the electrical signal passing through the motor. The at least one operating parameter of the motor determined by the electronic device may include the current drawn by the motor and/or the voltage drop across the motor.

The electrical signal may comprise a plurality of spaced apart pulses.

The electronic device may include a circuit board containing electronic circuitry which is operable to apply the at least one operating parameter to the motor. The electronic circuitry may be operable to provide bi-directional drive of the motor.

The motor may be operable via one or more switches. The switches may be actuated by residual movement of the wearer of the prosthesis or orthosis, wrist and/or shoulder movement of the wearer of the prosthesis or orthosis, or the like. Alternatively, or additionally, the motor may be operable via signals derived from the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest, or the like.

The at least one operating condition of the component may include one or more of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to determine an instantaneous operating condition of the component, be operable to determine an historic operating condition of the component. That is, the electronic device may be operable to determine historical actions performed by the component. From a knowledge of the instantaneous operating condition of the component and a knowledge of the historical operating conditions of the component the electronic device may be further operable to determine a change in any of the conditions, an average of any of the conditions, a forecasted or requested operating condition.

The at least one operating condition of the component may also include the relative position of the component. The relative position of the component may be one dimensional, two dimensional or three dimensional. The operating condition of the component may also include the angle of the component, or a part thereof, to a reference plane, axis or point. The operating condition of the component may also include the distance between at least two components, such as a finger and thumb. The position of the component may be determined from a knowledge of the starting position or end position of the component, the duration of applied operating signal and the speed of travel of the component.

The at least one operating condition of the component may also include conditions derived from any of the above-referenced conditions, such as a change in any of the conditions, or an average of any of the conditions.

The at least one operating condition of the component may also include one or more previous operating conditions, one or more forecasted and/or requested operating conditions.

The at least one operating condition of the component may include a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The operating conditions described above may relate to the component as a whole or at least part of the component.

The electronic device may be operable to determine the instantaneous electrical signal applied to the motor. The electronic device may be operable to determine the instantaneous current and/or voltage applied to the motor. The electronic device may be operable to determine the instantaneous current drawn by the motor and/or the voltage drop across the motor. The current drawn by the motor for any applied operating voltage is dependent upon the load placed on the motor. The current drawn by the motor thus varies with respect to load placed thereupon.

The electronic device may include a circuit board containing electronic circuitry which is operable to measure the instantaneous operating parameter of the motor. The electronic circuitry may include a current and/or voltage measurement circuit.

The electronic device may include a memory device operable to store the predetermined operating profile of the motor and component.

The electronic device may include firmware operable to map the determined at least one instantaneous operating parameter of the motor to the predetermined operating profile of the motor and component. The electronic device may include firmware operable to compare the determined at least one instantaneous operating parameter of the motor with the predetermined operating profile of the motor and component.

The electronic device may include firmware operable to determine the at least one instantaneous operating condition of the component from the predetermined operating profile of the motor and component. The firmware may include a computer program stored in the memory of the firmware.

The predetermined operating profile of the motor and component may include one or more data sets representative of one or more operating parameter inputs to the motor and one or more resulting operating condition outputs of the component. The operating profile of the motor and component may be obtained by characterising the operation of the component as a function of operating parameter inputs to the motor. The operating profile of the motor and component may include one or more data sets representative of the instantaneous operating parameter of the motor as a function of the instantaneous operating condition of the component.

The predetermined operating profile of the motor and component may include one or more data sets representative of at least one of the following operating conditions of the component: initial movement, contact of the component with a surface, slipping or sliding of the component with a surface, acceleration, deceleration, average speed, instantaneous speed, amount of extension, amount of flexion, and force applied by the component to a surface; and corresponding operating parameters of the motor. The predetermined operating profile of the motor and component may include one or more data sets representative of the instantaneous operating conditions of the component listed above and one or more of the instantaneous operating parameters of the motor.

The predetermined operating profile of the motor and component may be obtained by characterising the operation of the motor as a function of one or more operating conditions of the component. The component may be instructed to perform one or more of the above-listed operating conditions and the resulting operating parameters of the motor measured. The current drawn by the motor and/or the voltage drop across the motor may be determined as the component carries out its instructed task. This characterising of the motor and component may be carried out over one or more of the above-listed operating conditions of the component.

The predetermined operating profile of the motor and component may be determined by a mathematical model based on the one or more operating parameter inputs to the motor and the one or more resulting operating condition outputs of the component. The mathematical model may be a mathematical function, numerical mapping, or the like. The mathematical model may be a neural network, an artificial neural network, decision tree (DT), support vector Machine (SVM), logistic regression (LR), other such "machine learning" techniques.

The electronic device may be further operable to produce an output signal indicative of the determined at least one instantaneous operating condition of the component.

The electronic device may be operable to produce an output signal indicative of one or more of the determined instantaneous operating conditions in the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to produce an output signal indicative of one or more determined instantaneous operating conditions of the component, be operable to produce an output signal indicative of one or more historic operating conditions of the component. That is, the electronic device may be operable to produce an output signal indicative one or more historical actions performed by the component. From a knowledge of the instantaneous operating condition of the component and a knowledge of the historical operating conditions of the component the electronic device may be further operable to produce an output signal indicative of a change in any of the conditions, an average of any of the conditions, a forecasted or requested operating condition.

The electronic device may be operable to produce an output signal indicative of the relative position of the component. The relative position of the component may be one dimensional, two dimensional or three dimensional. The electronic device may be operable to produce an output signal indicative of the angle of the component, or a part thereof, to a reference plane, axis or point. The electronic device may be operable to produce an output signal indicative of the distance between at least two components, such as a finger and thumb.

The electronic device may be operable to produce an output signal indicative of conditions derived from any of the above-referenced conditions, such as a change in any of the conditions, or an average of any of the conditions.

The electronic device may be operable to produce an output signal indicative of one or more previous operating conditions, one or more forecasted and/or requested operating conditions.

The electronic device may be operable to produce an output signal indicative of a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may be further operable to produce an output signal indicative of a plurality of determined instantaneous operating conditions of the component.

The output signal may be indicative of a general operating condition of the component. The general operating condition of the component may include one ore more modes of operation and/or configurations.

The electronic device may be further operable to produce an output signal which is indicative of a requested operating condition of the component from the wearer of the prosthesis or orthosis. The electronic device may be further operable to produce an output signal which is indicative of a completed operating condition of the component from the wearer of the prosthesis or orthosis.

The electronic device may be further operable to use the output signal together with the operating parameters of the motor in a control strategy for the operation of the component. The electronic device may be further operable to use the output signal together with the operating parameters of the motor to control the operation of the component. For example, the output signal may indicate the relative position of the component and the electronic device may modify the operating parameter of the motor based on the output signal to achieve a requested position of the component, or the output signal may indicate the force exerted by the component on an object and the electronic device may modify the operating parameter of the motor based on the output signal to achieve a requested force from the component.

Additionally, or alternatively, the electronic device may be further operable to communicate the output signal to the wearer of the prosthesis or orthosis.

The output signal may be communicated to the wearer of the prosthesis or orthosis visually, kinaesthetically, aurally or neurally.

The output signal may be communicated to the wearer of the prosthesis or orthosis in one or more combinations of the above forms of communication.

The output signal is thus fed back to the wearer of the prosthesis or orthosis. The mode of feedback to the wearer of the prosthesis or orthosis may include vibrotactile or electrotactile.

The output signal may be fed back to the wearer of the prosthesis or orthosis at a stump, arm or healthy hand, shoulder, neck, foot, tongue, or the like.

In this arrangement the wearer of the prosthesis or orthosis receives a signal from the electronic device which indicates to them an instantaneous operating condition of the component. Thus, for example, the wearer of the prosthesis or orthosis receives a feedback signal from the prosthesis or orthosis which indicates the current force being applied by the component to a surface or object. The wearer therefore knows if the current force being applied to the surface or object is suitable for their needs, or if a greater or lesser force is required. For example, if the wearer is trying to push a button with the component of the prosthesis, they will receive a feedback signal which indicates to them if the component is pressing against the button with sufficient force to allow the button to be depressed. Also, if the wearer is trying to move an object with the component of the prosthesis, they may receive a feedback signal which indicates to them if the component is pushing, pulling, squeezing or lifting the object with sufficient force to allow the object to be moved.

This is just one example of the information which may be fed back to the wearer. It should be appreciated that the output signal fed back to the wearer of the prosthesis or orthosis may include more than one instantaneous operating condition of the component.

The prosthesis or orthosis may comprise a plurality of moveable components, with each component having a motor and electronic device.

Alternatively, the prosthesis or orthosis may comprise a plurality of moveable components, with each motor having a motor, but only a single electronic device. In this arrangement the electronic device may be operable to determine the instantaneous operating parameters of each motor, map the instantaneous operating parameter of each motor to a predetermined operating profile of each motor and component, and determine the instantaneous operating condition of each component from the predetermined operating profile of each motor and component.

The prosthesis or orthosis may comprise one or more first components acting as fingers and second component acting as a thumb. In this arrangement the electronic device may be further operable to determine the grasp aperture between the fingers and thumb and undesired movement between the component and an object, i.e. a slip condition, between the fingers and thumb when each component is bearing against a surface or object. The grasp aperture and slip condition here being examples of operating conditions of the components.

According to a second aspect of the present invention there is provided a method of operating a prosthesis or orthosis having a moveable component, a motor operable to move the component, wherein the motor has at least one operating parameter, the application of which to the motor results in the component having at least one operating condition, and an electronic device, the method comprising the steps of:

applying at least one operating parameter to the motor; and using the electronic device to:
   determine at least one operating parameter of the motor; and
   determine at least one instantaneous operating condition of the component from a predetermined operating profile of the motor and component and the determined at least one operating parameter of the motor, the predetermined operating profile of the motor and component being based on one or more operating parameter inputs to the motor and one or more resulting operating condition outputs of the component.

The electronic device may be operable to determine at least one instantaneous operating parameter of the motor.

The predetermined operating profile of the motor and component may be based on a plurality of operating parameter inputs to the motor and a plurality of resulting operating condition outputs of the component.

The motor may be located inside the component.

The component may be a digit of a hand prosthesis. The component may be a finger or a thumb member of hand prosthesis. The motor may be located inside the digit of the hand prosthesis.

The component may be moveable with respect to a support body of the prosthesis or orthosis. The component may rotate and/or pivot with respect to the support body of the prosthesis or orthosis.

The motor may be an electric motor. The motor may be a direct current motor. The motor may be an AC motor, a DC motor, a brushed or brushless motor, a servo motor, a stepper motor, a linear motor or a worm gear motor.

The at least one operating parameter of the motor may include an electrical signal. The electrical signal may be in the form of an applied electrical current and/or voltage.

The at least one operating parameter of the motor may include the electrical signal passing through the motor. The at least one operating parameter of the motor determined by the electronic device may include the current drawn by the motor and/or the voltage drop across the motor.

The electrical signal may comprise a plurality of spaced apart pulses.

The electronic device may include a circuit board containing electronic circuitry which is operable to apply the at least one operating parameter to the motor. The electronic circuitry may be operable to provide bi-directional drive of the motor.

The motor may be operable via one or more switches. The switches may be actuated by residual movement of the wearer of the prosthesis or orthosis, wrist and/or shoulder movement of the wearer of the prosthesis or orthosis, or the like. Alternatively, or additionally, the motor may be operable via signals derived from the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest, or the like.

The method may comprise the further step of using residual movement of the wearer of the prosthesis or orthosis, wrist and/or shoulder movement of the wearer of the prosthesis or orthosis to apply the at least one operating parameter to the motor. The method may comprise the further step of using signals derived the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest to apply the at least one operating parameter to the motor.

The at least one operating condition of the component may include one or more of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to determine an instantaneous operating condition of the component, be operable to determine an historic operating condition of the component. That is, the electronic device may be operable to determine historical actions performed by the component. From a knowledge of the instantaneous operating condition of the component and a knowledge of the historical operating conditions of the component the electronic device may be further operable to determine a change in any of the conditions, an average of any of the conditions, a forecasted or requested operating condition.

The at least one operating condition of the component may also include the relative position of the component. The relative position of the component may be one dimensional, two dimensional or three dimensional. The operating condition of the component may also include the angle of the component, or a part thereof, to a reference plane, axis or point. The operating condition of the component may also include the distance between at least two components, such as a finger and thumb.

The at least one operating condition of the component may also include conditions derived from any of the above-referenced conditions, such as a change in any of the conditions, or an average of any of the conditions.

The at least one operating condition of the component may also include one or more previous operating conditions, one or more forecasted and/or requested operating conditions.

The at least one operating condition of the component may include a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The operating conditions described above may relate to the component as a whole or at least part of the component.

The electronic device may be operable to determine the instantaneous electrical signal applied to the motor. The electronic device may be operable to determine the instantaneous current and/or voltage applied to the motor. The electronic device may be operable to determine the instantaneous current drawn by the motor and/or the voltage drop across the motor. The current drawn by the motor for any applied operating voltage is dependent upon the load placed on the motor. The current drawn by the motor thus varies with respect to load placed thereupon.

The method may comprise the further step of using the electronic device to determine the instantaneous electrical signal applied to the motor.

The electronic device may include a circuit board containing electronic circuitry which is operable to measure the instantaneous operating parameter of the motor. The electronic circuitry may include a current and/or voltage measurement circuit.

The electronic device may include a memory device operable to store the predetermined operating profile of the motor and component.

The electronic device may include firmware operable to map the determined at least one instantaneous operating parameter of the motor to the predetermined operating profile of the motor and component. The electronic device may include firmware operable to compare the determined at least one instantaneous operating parameter of the motor with the predetermined operating profile of the motor and component.

The electronic device may include firmware operable to determine the at least one instantaneous operating condition of the component from the predetermined operating profile of the motor and component. The firmware may include a computer program stored in the memory of the firmware.

The predetermined operating profile of the motor and component may include one or more data sets representative of one or more operating parameter inputs to the motor and one or more resulting operating condition outputs of the component. The operating profile of the motor and component may be obtained by characterising the operation of the component as a function of operating parameter inputs to the motor. The operating profile of the motor and component may include one or more data sets representative of the instantaneous operating parameter of the motor as a function of the instantaneous operating condition of the component.

The predetermined operating profile of the motor and component may include one or more data sets representative of at least one of the following operating conditions of the component: initial movement, contact of the component with a surface, slipping or sliding of the component with a surface, acceleration, deceleration, average speed, instantaneous speed, amount of extension, amount of flexion, and force applied by the component to a surface; and corresponding operating parameters of the motor. The predetermined operating profile of the motor and component may include one or more data sets representative of the instantaneous operating conditions of the component listed above and one or more of the instantaneous operating parameters of the motor.

The predetermined operating profile of the motor and component may be obtained by characterising the operation of the motor as a function of one or more operating conditions of the component. The component may be instructed to perform one or more of the above-listed operating conditions and the resulting operating parameters of the motor measured. The current drawn by the motor and/or the voltage drop across the motor may be determined as the component carries out its instructed task. This characterising of the motor and component may be carried out over one or more of the above-listed operating conditions of the component.

The predetermined operating profile of the motor and component may be determined by a mathematical model based on the one or more operating parameter inputs to the motor and the one or more resulting operating condition outputs of the component. The mathematical model may be a mathematical function, numerical mapping, or the like. The mathematical model may be a neural network, an artificial neural network, decision tree (DT), support vector Machine (SVM), logistic regression (LR), other such "machine learning" techniques.

The electronic device may be further operable to produce an output signal indicative of the determined at least one instantaneous operating condition of the component.

The method may comprise the further step of using the electronic device to produce an output signal indicative of the determined at least one instantaneous operating condition of the component.

The electronic device may be operable to produce an output signal indicative of one or more of the determined instantaneous operating conditions in the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may, in addition to being operable to produce an output signal indicative of one or more determined instantaneous operating conditions of the component, be operable to produce an output signal indicative of one or more historic operating conditions of the component. That is, the electronic device may be operable to produce an output signal indicative one or more historical actions performed by the component. From a knowledge of the instantaneous operating condition of the component and a knowledge of the historical operating conditions of the component the electronic device may be further operable to produce an output signal indicative of a change in any of the conditions, an average of any of the conditions, a forecasted or requested operating condition.

The electronic device may be operable to produce an output signal indicative of the relative position of the component. The relative position of the component may be one dimensional, two dimensional or three dimensional. The electronic device may be operable to produce an output signal indicative of the angle of the component, or a part thereof, to a reference plane, axis or point. The electronic device may be operable to produce an output signal indicative of the distance between at least two components, such as a finger and thumb.

The electronic device may be operable to produce an output signal indicative of conditions derived from any of the above-referenced conditions, such as a change in any of the conditions, or an average of any of the conditions.

The electronic device may be operable to produce an output signal indicative of one or more previous operating conditions, one or more forecasted and/or requested operating conditions.

The electronic device may be operable to produce an output signal indicative of a combination of any of the group consisting of: initial movement, contact of the component with a surface, slipping or sliding of the component with a surface, acceleration, deceleration, average speed, instantaneous speed, amount of extension, amount of flexion, and force applied by the component to a surface.

The electronic device may be further operable to produce an output signal indicative of a plurality of determined instantaneous operating conditions of the component.

The method may comprise the further step of using the electronic device to produce an output signal indicative of a plurality of determined instantaneous operating condition of the component.

The output signal may be indicative of a general operating condition of the component. The general operating condition of the component may include one ore more modes of operation and/or configurations.

The method may comprise the further step of using the electronic device to produce an output signal indicative of a general operating condition of the component.

The electronic device may be further operable to produce an output signal which is indicative of a requested operating condition of the component from the wearer of the prosthesis or orthosis. The electronic device may be further operable to produce an output signal which is indicative of a completed operating condition of the component from the wearer of the prosthesis or orthosis.

The method may comprise the further step of using the electronic device to produce an output signal indicative of a requested operating condition of the component. The method may comprise the further step of using the electronic device to produce an output signal indicative of a completed operating condition of the component.

The electronic device may be further operable to use the output signal together with the operating parameters of the motor in a control strategy for the operation of the component. The electronic device may be further operable to use the output signal together with the operating parameters of the motor to control the operation of the component. For example, the output signal may indicate the relative position of the component and the electronic device may modify the operating parameter of the motor based on the output signal to achieve a requested position of the component, or the output signal may indicate the force exerted by the component on an object and the electronic device may modify the operating parameter of the motor based on the output signal to achieve a requested force from the component.

The method may comprise the further step of using the electronic device to use the output signal together with the operating parameters of the motor in a control strategy for the operation of the component.

Additionally, or alternatively, the electronic device may be further operable to communicate the output signal to the wearer of the prosthesis or orthosis.

The method may comprise the further step of using the electronic device to communicate the output signal to the wearer of the prosthesis or orthosis.

The output signal may be communicated to the wearer of the prosthesis or orthosis visually, kinaesthetically, aurally or neurally.

The output signal may be communicated to the wearer of the prosthesis or orthosis in one or more combinations of the above forms of communication.

The output signal is thus fed back to the wearer of the prosthesis or orthosis. The mode of feedback to the wearer of the prosthesis or orthosis may include vibrotactile or electrotactile.

The output signal may be fed back to the wearer of the prosthesis or orthosis at a stump, arm or healthy hand, shoulder, neck, foot, tongue, or the like.

In this arrangement the wearer of the prosthesis or orthosis receives a signal from the electronic device which indicates to them an instantaneous operating condition of the component. Thus, for example, the wearer of the prosthesis or orthosis receives a feedback signal from the prosthesis or orthosis which indicates the current force being applied by the component to a surface or object. The wearer therefore knows if the current force being applied to the surface or object is suitable for their needs, or if a greater or lesser force is required. For example, if the wearer is trying to push a button with the component of the prosthesis, they will receive a feedback signal which indicates to them if the component is pressing against the button with sufficient force to allow the button to be depressed. Also, if the wearer is trying to move an object with the component of the prosthesis, they may receive a feedback signal which indicates to them if the component is pushing, pulling, squeezing or lifting the object with sufficient force to allow the object to be moved.

This is just one example of the information which may be fed back to the wearer. It should be appreciated that the output signal fed back to the wearer of the prosthesis or orthosis may include more than one instantaneous operating condition of the component.

The prosthesis or orthosis may comprise a plurality of moveable components, with each component having a motor and electronic device.

Alternatively, the prosthesis or orthosis may comprise a plurality of moveable components, with each motor having a motor, but only a single electronic device. In this arrangement the electronic device may be operable to determine the instantaneous operating parameters of each motor, map the instantaneous operating parameter of each motor to a predetermined operating profile of each motor and component, and determine the instantaneous operating condition of each component from the predetermined operating profile of each motor and component.

The method may comprise the further step of using the electronic device to determine the instantaneous operating parameters of each motor, map the instantaneous operating parameter of each motor to a predetermined operating profile of each motor and component, and determine the instantaneous operating condition of each component from the predetermined operating profile of each motor and component.

The prosthesis or orthosis may comprise one or more first components acting as fingers and second component acting as a thumb. In this arrangement the electronic device may be further operable to determine the grasp aperture between the fingers and thumb and undesired movement between the component and an object, i.e. a slip condition, between the fingers and thumb when each component is bearing against a surface or object. The grasp aperture and slip condition here being examples of operating conditions of the components.

Embodiments of the present invention will now be described by way of example only with reference to the following drawing, of which:

Figure 1:
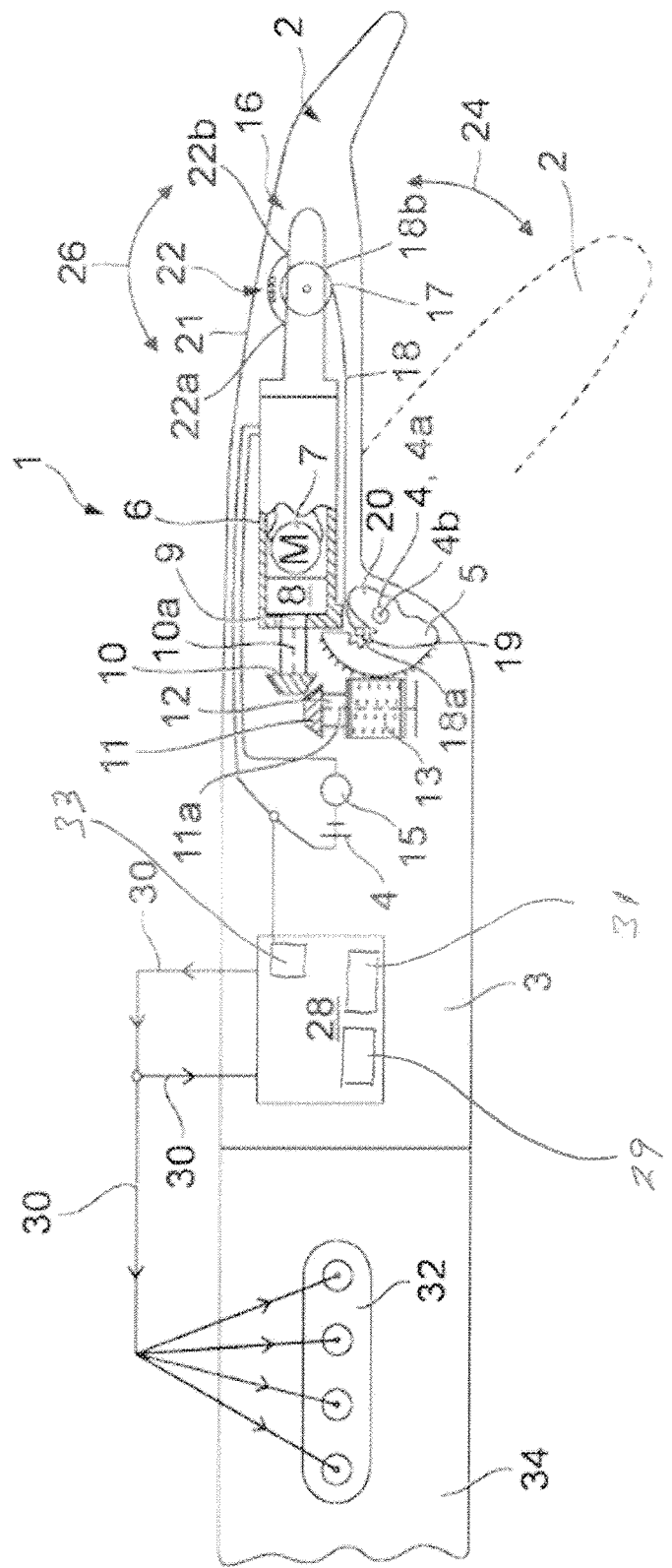
FIG. 1 is a partly cut-away view of a digit member of a prosthesis according to the present invention.

FIG. 1 illustrates a partly cut-away view of a hand prosthesis 1 having a finger 2 (an example of a moveable component or digit). The prosthesis 1 is securely fixed in use to a wearer's hand stump (see below) in a generally known manner by means of a socket component body (not shown). The prosthesis 1 has a main body 3 which has a spindle 4 on which a gear wheel 5 is fixedly mounted. The gear wheel 5 is of roughly semi-circular profile. The finger 2 extends generally tangentially with respect to the gear wheel 5. The finger 2 has a generally tubular housing 6, in which is mounted a motor 7 having a gearbox system 8. The gearbox system 8 provides for different torque—output drive speed ratios to be selected from a range of different ratios. Lugs (not shown) depend from the underside of the tubular housing 6 and are rotatably mounted to the spindle 4 to allow for rotation of the finger 2 in relation to the spindle 4 and gear wheel 5. The spindle 4 has a centre 4a which defines an axis 4b about which the finger 2 rotates. The housing 6 containing the motor 7 corresponds to the proximal phalanx of a finger and the joint formed between the spindle 4 and the lugs depending from the housing 6 correspond to the metacarpophalangeal (MCP) or knuckle joint of a finger.

A drive shaft 9 extends from the motor 7 and gearbox system 8. A first bevel gear 10 is mounted on the distal end of the drive shaft 9. A second bevel gear 11 is mounted within the prosthesis 1 such that an axis of rotation 11a of the second bevel gear 11 is at substantially 90 degrees to an axis of rotation 10a of the first bevel gear 10.

The gear ratio of the first and second bevel gears 10, 11 is substantially 1:1, although the gear ratio can be readily changed by known means. The second bevel gear 11 is mounted on a shaft 12, which also includes a worm 13. The worm 13 is located such that it engages with a toothed, curved peripheral edge of the gear wheel 5. As illustrated in FIG. 1, the worm 13 extends laterally to the housing 6 at an angle of substantially 90 degrees. The worm 13 and the gear wheel 5 have a 25:1 reduction ratio.

In the embodiment illustrated here the worm 13 is located in the prosthesis 1 such that it is outside the housing 6. Thus the worm 13 is located within the main body 3 of the prosthesis 1 and not the finger 2, even though the prosthesis 1 is structured such that the worm 13 moves with the housing 6 upon operation of the finger 2, as described below. However, it should also be appreciated that in other embodiments of the prosthesis the worm 13 may be located in the housing 6.

In the embodiment illustrated and described here the motor 7 is a permanent magnet DC motor having a substantially linear relationship between torque and drive current. In normal use the motor rotates at around 21,000 rpm. The motor is powered by small rechargeable batteries 14, which may be mounted remotely of the prosthesis 1.

The motor 7 is operable to move the finger 2, as described in more detail below. The motor 7 operates by application of an appropriate electrical signal, i.e. a current/voltage signal (an example of at least one operating parameter of the motor).

The motor 7 is controlled by means of switches 15, which are actuated by known means, e.g. residual digit movement or wrist/shoulder movement of the wearer of the prosthesis 1. Alternatively, or in addition, control may be via signals derived from electromyographic (EMG) activity of residual muscle actions of the wearer of the prosthesis 1, or pressure sensitive resistors on the wearer of the prosthesis 1, or signals derived from one or more neural implants in the wearer of the prosthesis 1, or EMG activity from reinnervated muscles, muscles of the feet and/or chest, or the like.

Figure 2:
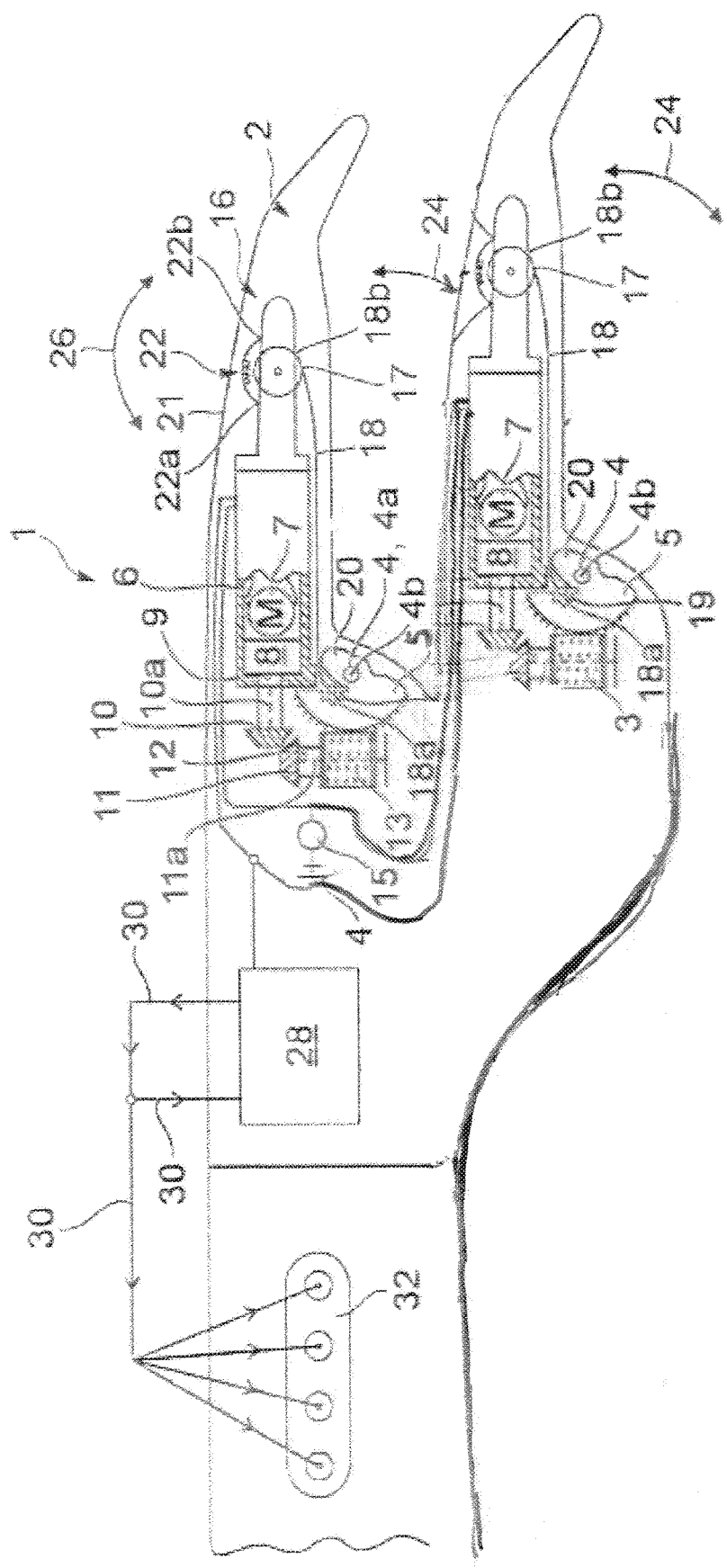
FIG. 2 is a diagram with two embodiments of the digit of FIG. 1 incorporated into two digits of a hand prosthesis.

In forms of the invention in which the prosthesis 1 comprises a plurality of other digits, i.e. a thumb and one or more other fingers (FIG. 2), control by known means may provide for independence of movement of the digits or groups of digits. In the case of a finger or a thumb the motor 7 has low speed, high torque characteristics.

The finger 2 has a finger tip portion 16 corresponding to the middle and distal phalanges of a finger, which forms with the distal end of the housing 6 a proximal joint 17 corresponding to a proximal intermediate phalangeal (PIP) joint of a finger. Arrow 24 represents movement of the finger 2 about axis 4*b* (i.e. the MCP joint) and arrow 26 represents movement of finger tip portion 16 about PIP joint 17. An inextensible belt or chord 18 is attached at a first end 18*a* to the gear wheel 5 in an aperture 19 provided in the gear wheel 5. The belt or chord 18 passes over a protrusion 20 formed on the gear wheel 5 and attaches at a second end 18*b* to the finger tip portion 16. A helical spring 22 is connected at one end 22*a* to the end of housing 6 and at a second opposing end 22*b* to the finger tip portion 16. The prosthesis is clad in a known manner with an overlay 21 of silicone rubber or the like to provide an aesthetically acceptable appearance which is as similar as practicable to a normal hand.

The prosthesis 1 further comprises an electronic device 28 containing electronic circuitry, which is operable to control the operation of the motor 7. That is, the electronic device 28 is operable to apply the current/voltage signals to the motor 7 to control the operation thereof. The electronic device 28 comprises an H-bridge, or the like, which is used to provide bi-directional drive of the motor 7.

The electronic device 28 includes a digital signal controller device (not shown) and a memory device (not shown). The control processes of the prosthesis 1 performed by the electronic device 28 are embodied in firmware, which is stored in and executed on the digital signal controller device and the memory device.

The electronic device 28 includes a digital signal controller device 29 and a memory device 31. The control processes of the prosthesis 1 performed by the electronic device 28 are embodied in firmware, which is stored in and executed on the digital signal controller device 29 and the memory device 31.

The electronic device 28 also comprises a current measurement circuit 33, which is configured to measure current drawn through the H-bridge and, therefore, motor 7. It should be appreciated that the electronic device 28 may additionally, or alternatively, comprise a voltage measurement circuit, which is configured to measure the voltage drop across the H-bridge and, therefore, motor 7.

In use, the wearer of the prosthesis 1 actuates the finger 2 by one of the means described above, e.g. by way of EMG activity of residual muscle actions. Operation of the motor 7 in response to actuation causes rotation of the first bevel gear 10, which rotates the second bevel gear 11 together with the worm 13. As the worm 13 rotates it progresses around the peripheral surface of the fixed gear wheel 5 either clockwise or anti-clockwise depending on the direction of rotation of the motor 7. This moves the finger 2 about the axis 4*b* in the direction indicated by arrow 24. As the finger 2 moves about axis 4*b* in a downward direction the distance between the point of attachment of the belt 18 in aperture 19 of the worm gear wheel 5 and the proximal joint 17 reduces. This is because the aperture 19 is offset from the axis 4*b* of the gear wheel 5 as shown in FIG. 1.

As the distance reduces the fixed length belt 18 pulls the finger tip portion 16 against the bias of the helical spring 22 to rotate the finger tip portion 16 clockwise in relation to the rest of the finger 2. Upon reversal of the direction of rotation of the finger 2 about the axis, i.e. movement of the finger 2 upwards, tension is released on the belt 18 and the spring 22 exerts a bias on the finger tip portion 16 to return the finger tip portion 16 to the extended position illustrated in FIG. 1.

The movement of the finger 2 as a result of the above-described operation of the motor 7 is an example of the finger 2 having at least one operating condition. However, operating conditions of the finger 2 may also include: initial movement, contact of the finger 2 with a surface, slipping or sliding of the finger 2 with a surface, acceleration, deceleration, average speed, instantaneous speed, amount of extension, amount of flexion, and force applied by the finger 2 to a surface. It should also be appreciated that the operating condition of the finger 2 may include any combination of the group consisting of: initial movement, contact of the finger 2 with a surface, slipping or sliding of the finger 2 with a surface, acceleration, deceleration, average speed, instantaneous speed, amount of extension, amount of flexion, and force applied by the finger 2 to a surface. It should also be appreciated that the operating condition of the finger 2 may include a plurality of any of the group consisting of: initial movement, contact of the finger 2 with a surface, slipping or sliding of the finger 2 with a surface, acceleration, deceleration, average speed, instantaneous speed, amount of extension, amount of flexion, and force applied by the finger 2 to a surface.

Furthermore, the operating condition of the finger 2 may also include a general operating condition of the finger 2, e.g. "on/off", or a mode of operation and/or configuration of the finger 2. The mode of operation and/or configuration of the finger 2 may include different types of grasps, such as a "power" grasp or a "precision" grasp. These different modes of operation have different operating characteristics.

The relationship between the instantaneous current/voltage signal applied to the motor 7 and the current/voltage drawn by or dropped across the motor 7 (i.e. motor load) is a complex function of, inter alia, the current/voltage signal applied to the motor 7, the hardness of the surface or object which the finger 2 impinges upon, finger movements and mechanical leverage, nonlinearities and variability in fabrication of gearing, location of contact/load on finger 2.

The memory device of the electronic device 28 has stored thereupon a predetermined operating profile of the motor 7 and finger 2. The operating profile of the motor 7 and finger 2 is based on one or more operating parameters inputs to the motor 7 and one or more operating condition outputs of the finger 2. That is, the operating profile of the motor 7 and finger 2 is based on one or more current/voltage inputs to the motor 7 and one or more operating condition outputs of the finger 2, such as one of those referenced above.

The operating profile of the motor 7 and finger 2 includes a plurality of data sets representative of a plurality of operating parameter inputs to the motor 7 and a plurality of resulting operating condition outputs of the finger 2. The operating profile of the motor 7 and finger 2 is obtained by characterising the operation of the finger 2 as a function of current/voltage input to the motor 7. The operating profile of the motor 7 and finger 2 also includes a plurality of data sets representative of the instantaneous current/voltage inputs to the motor 7 as a function of the instantaneous operating condition of the finger 2.

The operating profile of the motor 7 and finger 2 also includes a plurality of data sets representative of at least one of the following operating conditions of the finger 2: initial movement, contact of the finger 2 with a surface, slipping or sliding of the finger 2 with a surface, acceleration, deceleration, average speed, instantaneous speed, amount of extension, amount of flexion, and force applied by the finger 2 to a surface; and corresponding current/voltage inputs to the motor 7.

The operating profile of the motor 7 and finger 2 is, for example, obtained by characterising the operation of the motor 7 as a function of one or more operating conditions of the finger 2. The finger 2 is instructed by the wearer, or an external control program, to perform one or more of the above-listed operating actions (conditions) and the resulting current/voltage operating parameters of the motor 7 are measured. The current drawn by the motor 7 and/or the voltage drop across the motor 7 is determined as the finger 2 carries out its instructed task. This characterising of the motor 7 and finger 2 is carried out over a plurality of operating conditions of the finger 2.

The operating profile of the motor 7 and finger 2 is determined by a mathematical model based on the above-described motor inputs and finger outputs. The mathematical model may be a mathematical function, numerical mapping, or the like. The mathematical model may be a neural network, an artificial neural network, decision tree (DT), support vector Machine (SVM), logistic regression (LR), other such "machine learning" techniques.

The electronic device 28 is further operable to determine at least one instantaneous operating condition of the finger 2 from the predetermined operating profile of the motor 7 and finger 2 stored on the memory device and the determined current/voltage operating parameters of the motor 7. That is, the electronic device 28 is capable of determining from a measurement of the current/voltage parameter of the motor 7 the instantaneous operating condition of the finger 2.

The electronic device 28 does this by firstly measuring the current/voltage drawn by, or dropped across, the motor 7; then mapping, or comparing, the measured current voltage to the predetermined operating profile of the motor 7 and finger 2 stored on the memory device. From the operating profile of the motor 7 and finger 2 the electronic device 28 is able to determine the instantaneous operating condition of the finger 2. For any given operating condition of the finger 2, such as those recited above, the motor 7 has a current/voltage "signature". The electronic device 28 determines the current/voltage signature of the motor 7 and then uses the operating profile to determine the operating condition of the finger 2 to which it relates.

The electronic device 28 includes firmware which is operable to perform the mapping of the measured current voltage to the predetermined operating profile of the motor 7 and finger 2.

The electronic device 28 may measure the instantaneous current/voltage operating parameter of the motor 7 or the electronic device 28 may, for example, take an average current/voltage measurement of the motor 7. The electronic device 28 is required to be operable such that it is capable of determining the current/voltage "signatures" of the motor.

The electronic device 28 is also operable to determine an historic operating condition of the finger 2. That is, the electronic device 28 is capable of accessing historical information regarding the operation of the finger 2. This information may, for example, be stored on the memory device. From a knowledge of the instantaneous operating condition of the finger 2 and a knowledge of the historical operating conditions of the finger 2 the electronic device 28 is further operable to determine a change in any of the conditions of the finger 2, an average of any of the conditions of the finger 2, a forecasted or requested operating condition of the finger 2.

The electronic device 28 is further operable to produce an output signal 30 which is indicative of the instantaneous operating condition of the finger 2. Furthermore, the electronic device 28 is also operable to produce an output signal which is indicative of an historic operating condition of the finger 2. This is a result of the electronic device 28 being capable of determining both the instantaneous operating condition of the finger 2 and the historic operating condition of the finger 2. The output signal 30 may represent any of the operating conditions of the finger 2 described above, including changes, averages, previous conditions, forecasted conditions or requested conditions.

The electronic device 28 is also operable to use the output signal 30 together with the current/voltage operating parameters of the motor 7 in a control strategy for the operation of the finger 2. In this arrangement the electronic device 28 uses the output signal 30 together with the current/voltage operating parameters of the motor 7 to control the operation of the motor 7. In this arrangement the output signal 30 is fed back to the electronic device 28 as in input thereto. The output signal 30 may, for example, indicate the relative position of the finger 2 and the electronic device 28 may modify the current/voltage operating parameters of the motor 7 based on the output signal 30 to achieve a requested position of the finger 2, or to correct for any error in a requested position of the finger 2. As a further example, the output signal 30 may indicate the force exerted by the finger 2 on an object and the electronic device 28 may modify the current/voltage operating parameters of the motor 7 based on the output signal 30 to achieve a requested force from the finger 2. Thus the output signal 30 may function with the electronic device 28 in a feedback control loop arrangement to modify the operation of the finger 2.

The above arrangement provides proportional linear control of the operation of the finger 2. That is, the wearer of the prosthesis 1 knows that there is a linear relationship between the EMG signal that they apply to the prosthesis 1 and, for example, the force applied by the finger 2 to an object or surface. This operation of the finger 2 is extremely advantageous to the wearer of the prosthesis 1. For example, this provides the wearer of the prosthesis 1 with increased confidence when handling delicate objects, particularly so when the prosthesis 1 includes a plurality of fingers 2 and a thumb component (see below).

Additionally, or alternatively, the electronic device 28 is operable to communicate the output signal 30 to the wearer of the prosthesis 1. That is, the electronic device 28 is operable to feedback an operating condition of the finger 2. Thus the wearer of the prosthesis 1 is able to receive operating information about the finger 2. For example, the wearer of the prosthesis 1 is able to know the force that the finger 2 is applying to an object.

The output signal 30 may be communicated to the wearer of the prosthesis 1 by, for example, any of the following means: visually, kinaesthetically, aurally or neurally.

In one arrangement the mode of feedback to the wearer of the prosthesis 1 may be vibrotactile. In this arrangement the wearer of the prosthesis 1 has a number of vibrotactors 32 (vibrating motors) mounted to, for example, their forearm 34 (stump). The output signal 30 is decoded (by, for example, the electronic device 28) to produce an operating mode for the vibrotactors 32. The operating mode for the vibrotactors 32 indicates to the wearer of the prosthesis 1 the operating condition of the finger 2. Due to the large number of operating conditions of the finger 2, there are clearly a large number of operating modes for the vibrotactors 32. Conditions of operation of the vibrotactors 32 may include amplitude, frequency, pulse width, period, number of pulses, period between pulses, patterns of operation between vibrotactors 32 etc. The wearer of the prosthesis 1 learns to recognise the modes of operation of the vibrotactors 32 and operating condition of the finger 2 by, for example, performing a number of tasks with the finger 2.

In one operating example the wearer of the prosthesis 1 receives a feedback signal from the prosthesis 1 which indicates the current force being applied by the finger 2 to a surface or object. The wearer therefore knows if the force being applied to the surface or object is suitable for their needs, or if a greater or lesser force is required. For example, if the wearer is trying to push a button with the finger 2 of the prosthesis 1, they will receive a feedback signal which indicates to them if the component is pressing against the button with sufficient force to allow the button to be depressed. Also, if the wearer is trying to move an object with the finger 2 of the prosthesis 1, they may receive a feedback signal which indicates to them if the component is pushing, pulling, squeezing or lifting the object with sufficient force to allow the object to be moved.

The above arrangement again provides proportional linear control of the operation of the finger 2 in the same manner as described above.

It should be appreciated that the output signal 30 fed back to the wearer of the prosthesis 1 may be indicative of a plurality of instantaneous operating conditions of the finger 2.

Although the prosthesis has been illustrated and described above as comprising a single finger 2, it should be appreciated that the prosthesis 1 may comprise a plurality of moveable fingers 2, with each finger 2 including a motor 7 and an electronic device 28, such that each finger 2 operates in the same manner described above. Alternatively, the prosthesis 1 may comprise a plurality of fingers 2, with each finger 2 having a motor 7, but only a single electronic device 28. In this arrangement the electronic device 28 is operable to determine the instantaneous operating parameters of each motor 7, map the instantaneous operating parameter of each motor 7 to a predetermined operating profile of each motor 7 and finger 2, and determine the instantaneous operating condition of each finger 2 from the predetermined operating profile of each motor 7 and finger 2.

The prosthesis 1 may comprise one or more moveable components 2 acting as fingers and a second component 2 acting as a thumb. In this arrangement the electronic device 28 is further operable to determine the grasp aperture between the fingers and thumb and undesired movement between the components 2 and an object, i.e. a slip condition, between the fingers and thumb when each component 2 is bearing against a surface or object. The grasp aperture and slip condition here being examples of operating conditions of the components 2.

Modifications and improvements may be made to the above without departing from the scope of the invention, for example, although the electronic device 28 has been described above as determining (measuring) the instantaneous operating parameter (current/voltage) of the motor 7, it should be appreciated that the electronic device 28 may be configured to determine (measure), or sample, the current/voltage operating parameters of the motor 7 over a period of time and, for example, take an average measurement.

Furthermore, although the above embodiment has been described with reference to a finger component of a hand prosthesis, it should be appreciated that the present invention is also applicable to moveable components on other forms of prosthesis, such as toes of a foot prosthesis, of moveable components of an orthosis. It should also be appreciated that the present invention is also applicable to any components which link, or interconnect, between moveable components of a prosthesis or orthosis.

Figure 3:
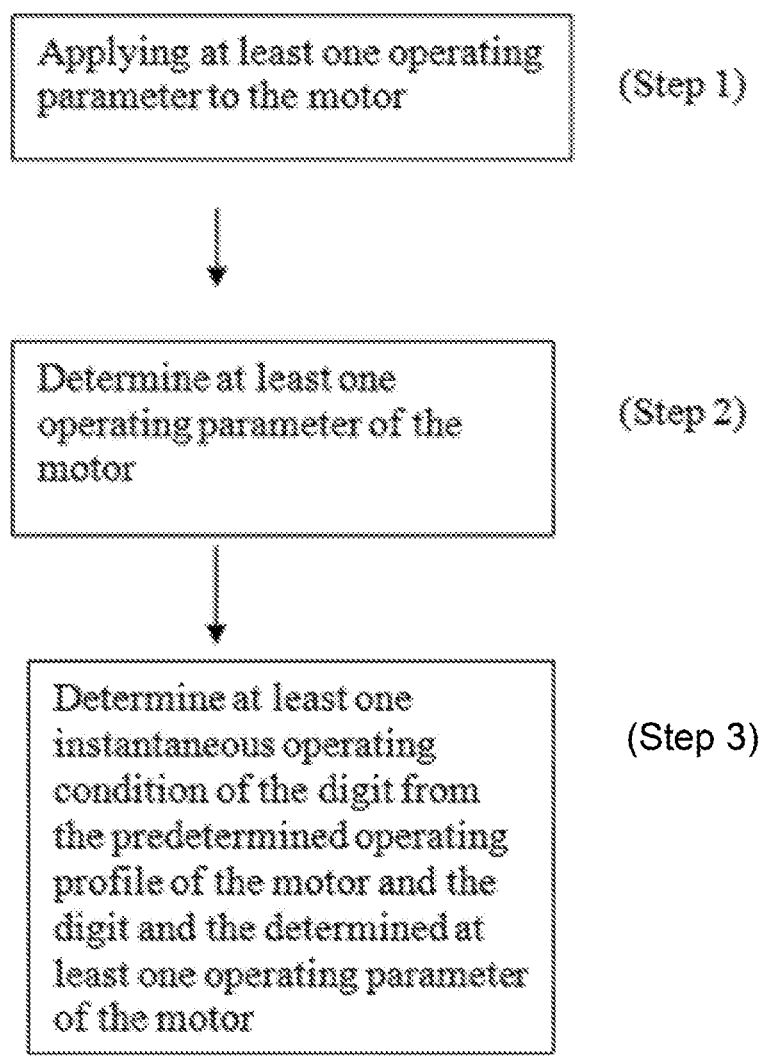
FIG. 3 is a flow diagram of an embodiment of the method of the invention.

In summary, the invention provides a method of operating a prosthesis or orthosis having a moveable digit, a motor operable to move the digit and an electronic device to control the movement of the digit. The motor has at least one operating parameter, the application of which to the motor results in the digit having at least one operating condition. In one embodiment, and referring to FIG. 3, the method comprises the steps of: applying at least one operating parameter to the motor (Step 1) and using the electronic device to determine at least one operating parameter of the motor (Step 2). The electronic device then determines (Step 3) at least one instantaneous operating condition of the digit from the predetermined operating profile of the motor and the digit and the determined at least one operating parameter of the motor, the predetermined operating profile of the motor and the digit being based on one or more operating parameter inputs to the motor and one or more resulting operating condition outputs of the digit.

The invention claimed is:

1. A prosthesis for attachment to an arm of a user, the prosthesis comprising:
    a thumb digit and a finger digit;
    a first electric motor operable to move the thumb digit in response to a first control signal, wherein actuation of the first electric motor results in the first electric motor drawing a first current from a power source and further results in at least one operating condition of a plurality of operating conditions of the thumb digit;
    a second electric motor operable to move the finger digit in response to a second control signal, wherein actuation of the second electric motor results in the second electric motor drawing a second current from the power source and further results in at least one operating condition of a plurality of operating conditions of the finger digit; and
    a controller configured to operate the first electric motor to move the thumb digit and operate the second electric motor to move the finger digit, the controller comprising:

memory storing an operating profile, the operating profile including a plurality of current values of the first electric motor, a plurality of current values of the second electric motor, the plurality of operating conditions of the thumb digit comprising at least a thumb slip condition, and the plurality of operating conditions of the finger digit comprising at least a finger slip condition, wherein the operating profile associates each of the plurality of current values of the first electric motor with a corresponding operating condition of the plurality of operating conditions of the thumb digit, wherein the operating profile further associates each of the plurality of current values of the second electric motor with a corresponding operating condition of the plurality of operating conditions of the finger digit, and a processor communicatively coupled to the memory and configured to:

communicate the first and second control signals to the first and second electric motors, respectively, wherein the first and second control signals cause the thumb digit and the finger digit to initiate a pinch grip, measure the first and second currents drawn from the power source, compare the first current with the plurality of current values of the first electric motor of the operating profile and compare the second current with the plurality of current values of the second electric motor of the operating profile, identify an overall slip condition between the thumb digit and the finger digit based at least in part on the comparisons, wherein the comparisons indicate that at least one of the first current corresponds to the thumb slip condition or the second current corresponds to the finger slip condition, and communicate an output signal indicative of the overall slip condition between the thumb digit and the finger digit to the user by way of vibrotactile feedback.

2. The prosthesis of claim 1, further comprising a plurality of other finger digits, wherein each finger digit of the plurality of other finger digits includes a third motor, and wherein the controller is further configured to individually operate each of the third motors associated with the plurality of other finger digits to individually move one or more of the other finger digits.

3. The prosthesis of claim 1, wherein at least one of the first motor or the second motor is a worm gear motor.

4. The prosthesis of claim 1, wherein at least one of the first motor or the second motor is a stepper motor.

5. The prosthesis of claim 1, wherein at least one of the first control signal or the second control signal is based on electromyographic activity of the user.

6. The prosthesis of claim 1, wherein the thumb slip condition corresponds to a change in the first current over a period of time.

7. The prosthesis of claim 6, wherein the thumb slip condition corresponds to a reduction in the first current over the period of time.

8. The prosthesis of claim 6, wherein the comparison of the first current with the plurality of current values of the first electric motor of the operating profile indicates the thumb digit is moving after transitioning from a resting position.

9. The prosthesis of claim 1, wherein the finger slip condition corresponds to a change in the second current over a period of time.

10. The prosthesis of claim 9, wherein the finger slip condition corresponds to a reduction in the second current over the period of time.

11. The prosthesis of claim 9, wherein the comparison of the second current with the plurality of current values of the second electric motor of the operating profile indicates the finger digit is moving after transitioning from a resting position.

12. The prosthesis of claim 1, wherein the overall slip condition indicates that at least one of the thumb digit or the finger digit is at least one of slipping or sliding with respect to a surface of an object gripped between the thumb digit and the finger digit.

13. The prosthesis of claim 1, further comprising:
a first bevel gear mounted on a drive shaft connected to the first electric motor;
a second bevel gear configured to engage with the first bevel gear; and
a worm gear mounted on a second shaft that includes the second bevel gear,
wherein operation of the first electric motor causes rotation of the first bevel gear, which rotates the second bevel gear together with the worm gear, wherein rotation of the worm gear causes movement of the thumb digit.

14. The prosthesis of claim 13, further comprising a gear wheel engaged with the worm gear, wherein the rotation of the worm gear causes rotation of the gear wheel.

15. A method of operating a prosthesis comprising a thumb digit, a finger digit, and a controller, the method comprising:

communicating a first control signal to a first motor, wherein the first motor draws a first current from a power source to move the thumb digit based on the first control signal;

communicating a second control signal to a second motor, wherein the second motor draws a second current from the power source to move the finger digit based on the second control signal;

measuring the first and second currents drawn from the power source;

comparing the first current with a plurality of first current values of the first motor of an operating profile, the operating profile including the plurality of first current values of the first motor and a plurality of first operating conditions of the thumb digit comprising at least a thumb slip condition, wherein the operating profile associates each of the plurality of first current values of the first motor with a corresponding first operating condition of the plurality of first operating conditions of the thumb digit;

comparing the second current with a plurality of second current values of the second motor of the operating profile, the operating profile further including the plurality of second current values of the second motor and a plurality of second operating conditions of the finger digit comprising at least a finger slip condition, wherein the operating profile further associates each of the plurality of second current values of the second motor with a corresponding second operating condition of the plurality of second operating conditions of the finger digit;

identifying an overall slip condition between the thumb digit and the finger digit based at least in part on at least one of the comparing the first current with the plurality of first current values of the first motor or the comparing the second current with the plurality of second current values of the second motor;

producing, by the controller, a vibrotactile output signal indicative of the overall slip condition between the thumb digit and the finger digit; and communicating the vibrotactile output signal by the controller to a user of the prosthesis using vibrotactile feedback.

16. The method of claim 15, wherein the prosthesis comprises a plurality of other finger digits, wherein each finger digit of the plurality of other finger digits includes a third motor controlled by the controller, the method further comprising communicating one or more third control signals to the third motors, wherein the third motors draw one or more third currents from the power source to move the plurality of other finger digits based on the one or more third control signals.

17. The method of claim 15, wherein at least one of the first motor or the second motor is a worm gear motor.

18. The method of claim 15, wherein at least one of the first motor or the second motor is a stepper motor.

19. The method of claim 15, wherein at least one of the first control signal or the second control signal is based on electromyographic activity of the user.

20. The method of claim 15, wherein the overall slip condition indicates that at least one of the thumb digit or the finger digit is at least one of slipping or sliding with respect to a surface of an object gripped between the thumb digit and the finger digit.

* * * * *